(12) United States Patent
Cramer

(10) Patent No.: US 8,504,302 B2
(45) Date of Patent: Aug. 6, 2013

(54) TEMPLATE CONSTRAINED FRAGMENT ALIGNMENT USED TO IDENTIFY FRAGMENTS OF SIMILAR SHAPE AND ACTIVITY IN DRUG DEVELOPMENT

(76) Inventor: Richard D. Cramer, Santa Fe, NM (US)

( * ) Notice: Subject to any disclaimer, the term of this patent is extended or adjusted under 35 U.S.C. 154(b) by 0 days.

(21) Appl. No.: 13/018,195

(22) Filed: Jan. 31, 2011

(65) Prior Publication Data

US 2011/0282910 A1    Nov. 17, 2011

Related U.S. Application Data

(60) Provisional application No. 61/299,913, filed on Jan. 29, 2010.

(51) Int. Cl.
*G06F 19/00* (2011.01)
*G01N 31/00* (2006.01)
*G06G 7/58* (2006.01)

(52) U.S. Cl.
USPC .................. 702/19; 702/22; 702/27; 703/11; 703/12

(58) Field of Classification Search
None
See application file for complete search history.

(56) References Cited

U.S. PATENT DOCUMENTS

2006/0195267 A1 * 8/2006 Nicholls .......................... 702/19

OTHER PUBLICATIONS

Cramer (Journal of Medicinal Chemistry 92003) vol. 46, pp. 374-388).*

* cited by examiner

*Primary Examiner* — Lori A Clow
(74) *Attorney, Agent, or Firm* — Laurence Weinberger

(57) ABSTRACT

The computational drug discovery method disclosed herein permits a user to specify a three dimensional representation of a molecular fragment derived from a query molecule involved in a drug interaction that then serves as a template to which fragments derived from molecules in database libraries may be aligned. The likely activity of the substitution of the fragment from the database library for the fragment from the query molecule may then be predicted by appropriate shape characterization and CoMFA analysis. The spatial three dimensional representation of the query fragment may be developed from binding data, crystallographic data, modeling data, or any other biophysical or biochemical technique.

3 Claims, 4 Drawing Sheets

Exact match flow chart

Exact match flow chart

Approximate match flow chart

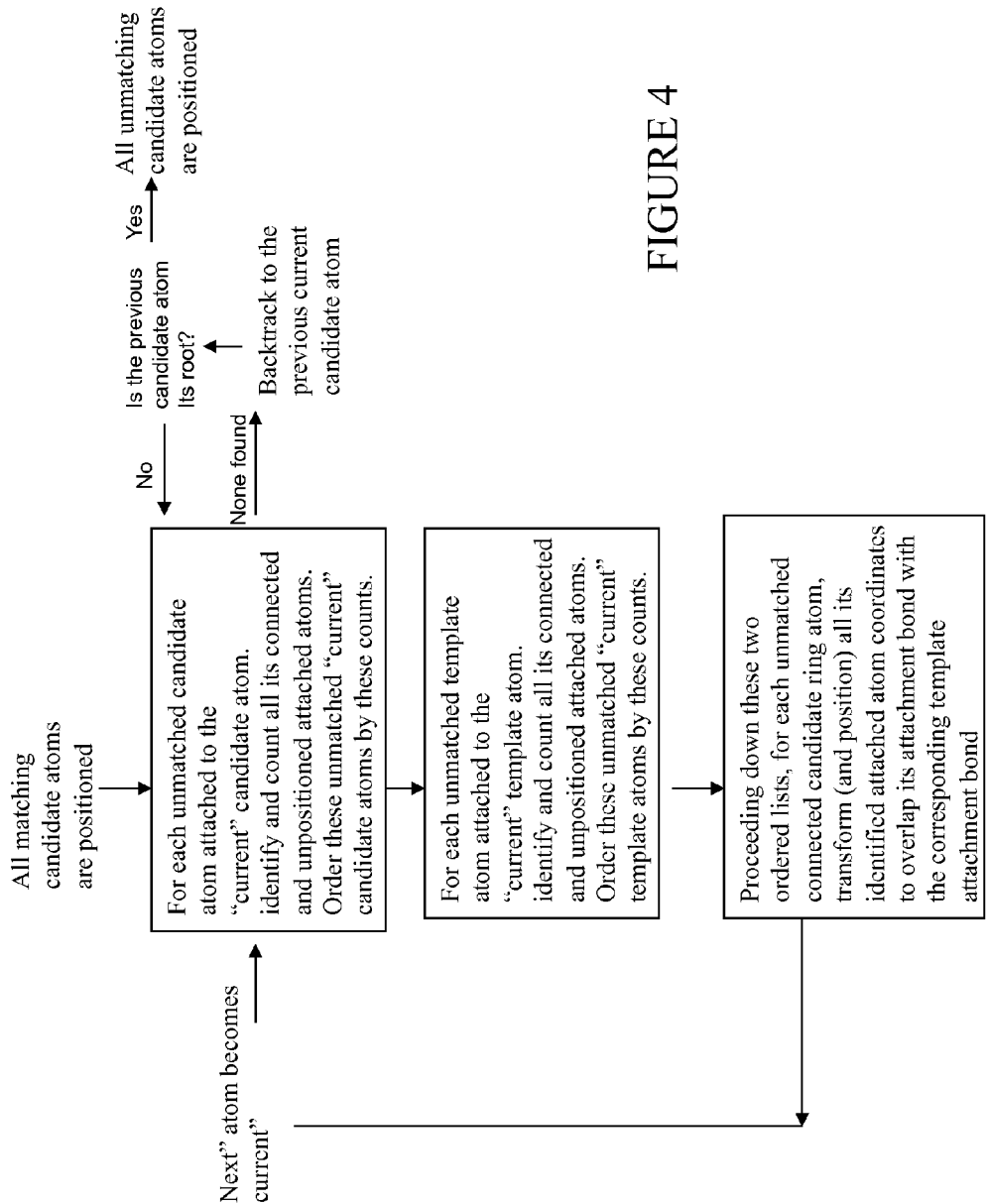

TEMPLATE CONSTRAINED FRAGMENT ALIGNMENT USED TO IDENTIFY FRAGMENTS OF SIMILAR SHAPE AND ACTIVITY IN DRUG DEVELOPMENT

Benefit of U.S. Provisional Application No. 61/299,913 filed on Jan. 29, 2010 is hereby claimed.

BACKGROUND OF THE INVENTION

1. Field of the Invention

This invention relates generally to a computer implemented drug discovery method. More specifically, the disclosed method permits a user to specify a three dimensional representation of an initial molecular fragment, which may be derived from binding data, crystallographic data, modeling data, or any other source, to identify additional molecular fragments having the same or similar three dimensional shape that may be incorporated into a drug molecule. The likely activity a molecule resulting from inclusion of the identified fragment can be predicted using a modified CoMFA technique as taught in U.S. Pat. No. 7,329,222.

2. Description of Related Art

During drug discovery, the final stage of lead optimization, the modification of an existing drug candidate to avoid liabilities ranging from toxicity issues to patent issues, is usually the most challenging and costly. Compounds are synthesized individually in relatively large quantities and may be tested in dozens of experimental assays. Often it is believed that only one fragment or R-group within a candidate structure is susceptible to modification and so the candidate structures are quite similar. Yet there will be thousands of reasonable alternative R-groups, and selection among these candidates will be increasingly effective as the means for predicting their biological affinities become more accurate. In such cases, the identification of molecular fragments similar in shape to molecular fragments derived from a known drug may be used to rank or propose candidate drug molecules. Alternate 3D representations of molecular fragments, such as topomerically aligned fragments, have been developed and have been successfully employed. In particular, the 3D QSAR technique known as Topomeric CoMFA has been highly successful especially when used in conjunction with a Virtual Library. The Topomeric CoMFA approach has been extended to searching and deriving predicted activities from fragments found in heterogeneous database libraries in U.S. patent application Ser. No. 12/045,511 using a fragmentation on-the-fly technique first taught in U.S. Pat. No. 7,330,793. Topomeric CoMFA techniques taught in these patent documents use fragments generated from molecules that have been determined to share activities at the same receptor to identify similarly shaped fragments in either a Virtual Library or heterogenous database library. However, as noted in U.S. Pat. No. 7,329,222 the use of a rule based (topomeric) procedure for aligning molecular fragments that lies at the heart of the Topomeric CoMFA methodology is not always applicable and may result in 3D fragment conformations that do not approximate those assumed by the fragment in an active molecule.

Importantly, there are many cases where it is believed that an alternative geometric alignment, based on knowledge about receptor site geometry gleaned from other sources, such as x-ray studies or ligand binding, might be more useful in computing a 3D QSAR such as CoMFA. For instance various biophysical and biochemical methods may indicate that a receptor binding site may possess particular geometric and chemical features. Alternatively, it may be desirable to seek alignments that overlay fragments from two or more structurally non-congeneric sets that may, for example, be known to bind to the same receptor. In these circumstances an alignment methodology would be advantageous that could align such structurally varied fragments to some user specified geometry or geometries.

The ultimate goal for the use of the present invention in drug discovery is to permit the drug developer to specify the three dimensional characteristics he/she believes are important for drug binding and to use those 3D characteristics to search for and identify appropriately shaped molecular fragments from molecular databases that may be incorporated into a drug design. The likely activity of such a drug may be predicted using the CoMFA technology as taught in U.S. Pat. No. 7,329,222 and further extended in U.S. patent application Ser. No. 12/045,511 where the alignments generated by the methods of the present invention are used in place of the rule based topomeric alignments.

DESCRIPTION OF FIGURES

FIG. 4 provides a flow chart of the methodology of the present invention for positioning the unmatching candidate atoms.

DETAILED DESCRIPTION OF THE INVENTION

Computational Chemistry Environment

Figure 1:
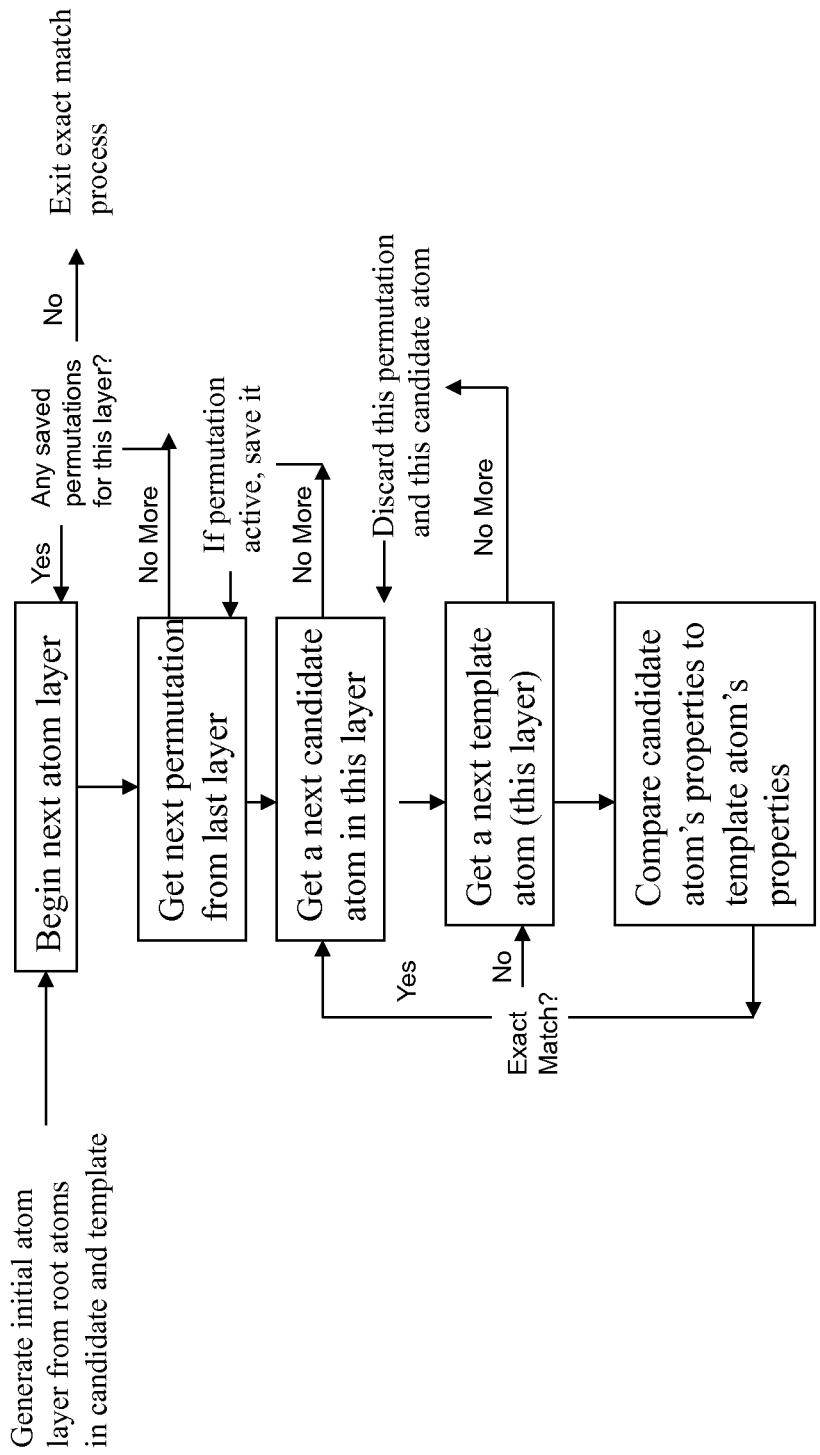
FIG. 1 provides a flow chart of the methodology of the present invention for an exact match analysis.

Software code to practice the present invention may written by one skilled in the art based upon the written description provided herein along with the corresponding detailed sequences provided in the flow charts of the accompanying Figures. In addition, software code provided as part of the disclosure of the United States patents listed below may be readily employed.

Generally, all calculations and analyses to perform the method of the present invention are implemented utilizing a specifically programmed computer employed in a modern computational chemistry environment using software designed to handle molecular structures and associated properties and operations. For purposes of the present application, such an environment is specifically referenced. In particular, the computational environment and capabilities of the SYBYL and UNITY software programs developed and marketed by Tripos, Inc. (St. Louis, Mo.) are specifically utilized. Software with similar functionalities to SYBYL and UNITY are available from other sources, both commercial and non-commercial, well known to those in the art.

The entire disclosure of the methods taught in the following patent documents U.S. Pat. No. 5,025,388, U.S. Pat. No. 5,307,287, U.S. Pat. No. 6,185,506, U.S. Pat. No. 6,240,374, U.S. Pat. No. 7,136,758, U.S. Pat. No. 7,184,893, U.S. Pat. No. 7,329,222, U.S. Pat. No. 7,330,793, and U.S. patent application Ser. No. 12/045,511 including the software code which forms a part of the patent disclosures are incorporated herein as if fully set forth.

A general purpose programmable digital computer with a fast CPU, ample amounts of memory, hard disk storage, display screens and printer outputs is required for the implementation of this invention. In performing the methods of this invention, representations of thousands of molecules, molecular structures, and fragments as well as other data may need to be stored simultaneously in the random access memory of the computer or in rapidly available permanent storage. The inventor uses any of a variety of currently available desktop or laptop computers meeting the above requirements and running Linux or Windows operating systems to practice this invention. Since a user of the method of the invention disclosed in this patent document can best understand and study the output and the computational shape analysis visually, especially given the enormous number and diversity of chemical structures analyzed, a display screen and system capable of visualizing and manipulating images of the three dimensional shapes is used. Chemists are generally some of the most visually oriented scientists when thinking about chemical structures and, therefore, a visualized output on a computer screen of the computational analysis matches their visual approach. Alternatively, selected results can be either captured as screen images or printed out on hard copy.

Template Constrained Fragment Alignment

The method described in the present patent document supplants the topomeric alignment method used in U.S. Pat. No. 7,330,793, and U.S. patent application Ser. No. 12/045,511 to align fragments for further shape characterization by interaction energies. The derived interaction energies (shape descriptors) are used to construct a CoMFA data table. After the CoMFA data table is constructed, predicted activities are generated as taught in the cited patent documents.

The present invention permits alignments of molecular fragments to one or more user supplied templates (alternative geometric alignments based on knowledge about receptor site geometry gleaned from other sources such as x-ray studies or ligand binding) that specify the types and three dimensional positions of all the atoms in one or more molecular fragments. Fragmentation of the query molecules that comprise the activity set as well as molecules examined in the database libraries is performed as taught in the cited patent documents.

The following description outlines the procedure for accomplishing such an alignment. For purposes of initial clarity in this patent disclosure, the fragment template will be considered not to have come from any fragment derived from a molecule in a congeneric series but from a template molecule selected by the user. However, it will be seen that any fragment from a congeneric series could be used as a template fragment as well. Thus, for purposes of the disclosure, reference to the template or template atoms will mean the externally specified 3D arrangement of atoms and their types. Reference to the candidate or candidate atoms will mean the arrangement of atoms and their types found in the fragments derived from the molecules in a congeneric series.

The purpose of the alignment procedure is to align each candidate fragment generated from the molecular series to the templates. (This procedure is in stark contrast to that used in topomeric CoMFA, where a rule based alignment was applied to all fragments in order to create a consistent alignment.) As with Topomeric CoMFA, when more than one fragment may be derived from a template molecule, a separate template for each fragment position may be provided to which fragments from that position are aligned. Once the common alignment is established, a useful CoMFA analysis may be performed. The results of the CoMFA analysis may be used to predict the likely activity of a drug candidate compound assembled from the fragments for subsequent synthesis.

Figure 3:
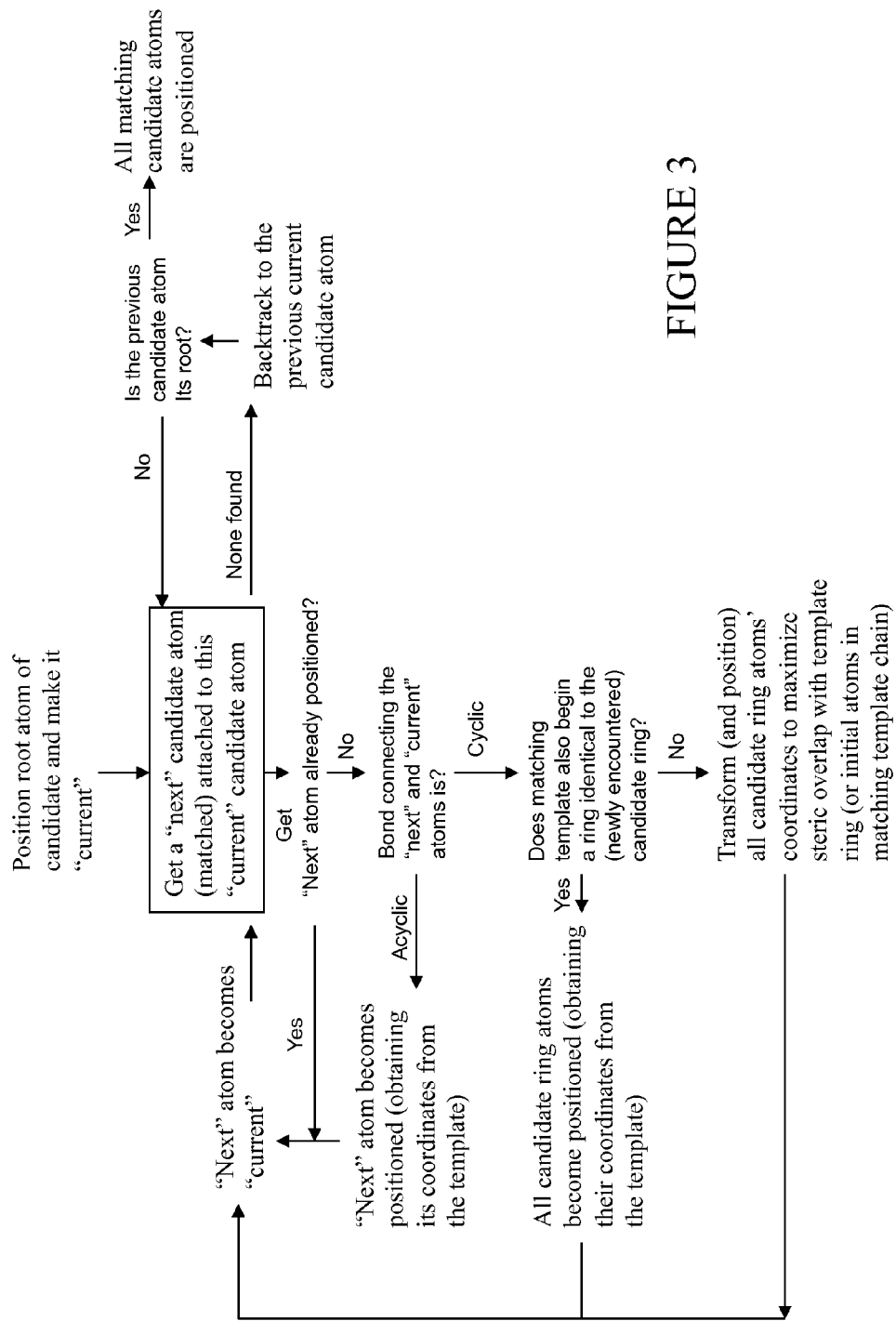
FIG. 3 provides a flow chart of the methodology of the present invention for positioning the matching candidate atoms.

The six stages of the overall alignment procedure may be summarized as follows:

1) The user fragments both the molecules in the congeneric series and the candidate template molecule and specifies the template fragment (or fragments) to which the candidate fragments are to be aligned.
2) 3D structures are generated for candidate fragments (as is done in topomer generation) using a 3D structure generating program such as Concord or Corina. Both template and candidate fragments are oriented by superimposing each fragment attachment bond onto a fixed vector position.
3) For both template and candidate, all atoms (and atom property/types) are identified excluding all hydrogen atoms
4) Atom-by-atom matches (identical atoms) between the template and the candidate are identified by serial/sequential traversals that start at the fragment root and end wherever no more matches exist along any given branch.
5) To align the candidate fragment, for atoms in the candidate fragment (excepting partial matches within rings) that match atoms in the template fragment, the coordinates of the matching template atoms are assigned to the candidate atoms. Position any atoms in the candidate fragment that do not have matching atoms in the template fragment so as to maintain their relative positions to those atoms in the candidate fragment that had matching atoms in the template fragment. For each alignment, apply the sequence of either FIG. 3 or FIG. 4 depending whether there was any kind of match (FIG. 3) or no match at all (FIG. 4).
6) For any branch that includes uncoordinated-copied atoms where the root of any branch will be a bond between a coordinate-copied and a coordinate-uncopied bond use the topomer alignment rules to place the atoms in the branch.
7) If there is more than one template, each template is prepared as described in steps 1-3, and step 4 is repeated for each template fragment. A single final alignment for the candidate fragment is automatically chosen from these results, typically as the template fragment that provides the largest number of atom-to-atom matches in step 4.

Steps 1) and 2) are accomplished as previously taught for Topomeric CoMFA (U.S. Pat. No. 7,329,222). In order to perform a template based alignment, it is necessary (step 3) to first identify all the atoms (and atom types) found in the candidate fragment that are identical to those found in the template. A complete matching (both atom type and atom properties are identical) is highly unlikely so that a partial match-identification method is also employed. After the atoms (and types) are identified, the candidate fragment is aligned.

In step 4), the identification of those atoms in the candidate fragment that match atoms in the template fragment is performed in two successive modes. Analysis in both modes proceeds from atom layer to atom layer. The first mode requires an exact match between candidate and template atom types and properties in each atom layer, and continues atom layer by atom layer until the next exact match criterion fails in a subsequent atom layer. The second mode, invoked when the first mode fails, requires only an approximate match between candidate and template atom types and properties. As the comparison goes forward, a list of those atoms that match at each layer is generated. The comparison process is implemented as shown in the flow chart of FIG. 1 as follows:

Exact Mode:
a) The process starts by matching the atom at the candidate fragment root to the atom at the template fragment root and proceeds by a breadth-first ("layered") processing of the remaining atoms in the candidate fragment. The list is updated to reflect each exact match.
b) For each non-hydrogen atom in the current layer of the candidate fragment for which an exact match has been identified, identify all its attached non-hydrogen atoms within the candidate fragment in the next atom layer.
c) Similarly, for the (previously identified) matching atom in the template fragment, identify all its attached non-hydrogen atoms in the next atom layer.
d) Since there may be more than one way to exactly match each of the candidate attached atoms onto the individual template attached atoms, including the possibility of more or fewer atoms at the next atom layer in either the template or candidate fragment, each of the atoms in the next candidate atom layer must be matched against each of the atoms in the next template atom layer until all permutations of candidate atoms to template atoms at that layer have been checked.
e) Every exactly matching permutation that is encountered in step d) is retained for further processing and extension, steps b) and c) then being applied to each permutation independently. Processing of an individual permutation ends whenever none of the atoms identified in step b exactly matches any of the atoms identified in step c.
f) The overall process stops when there are no more exact matches between any of the attached atoms in the candidate and to any of the attached atoms in the template, for any active permutation.

In "exact" mode, to accept a match between a candidate atom and a template atom, their atomic elements, and the type and ring status of their bonds to the previous atom layer must agree.

Figure 2:
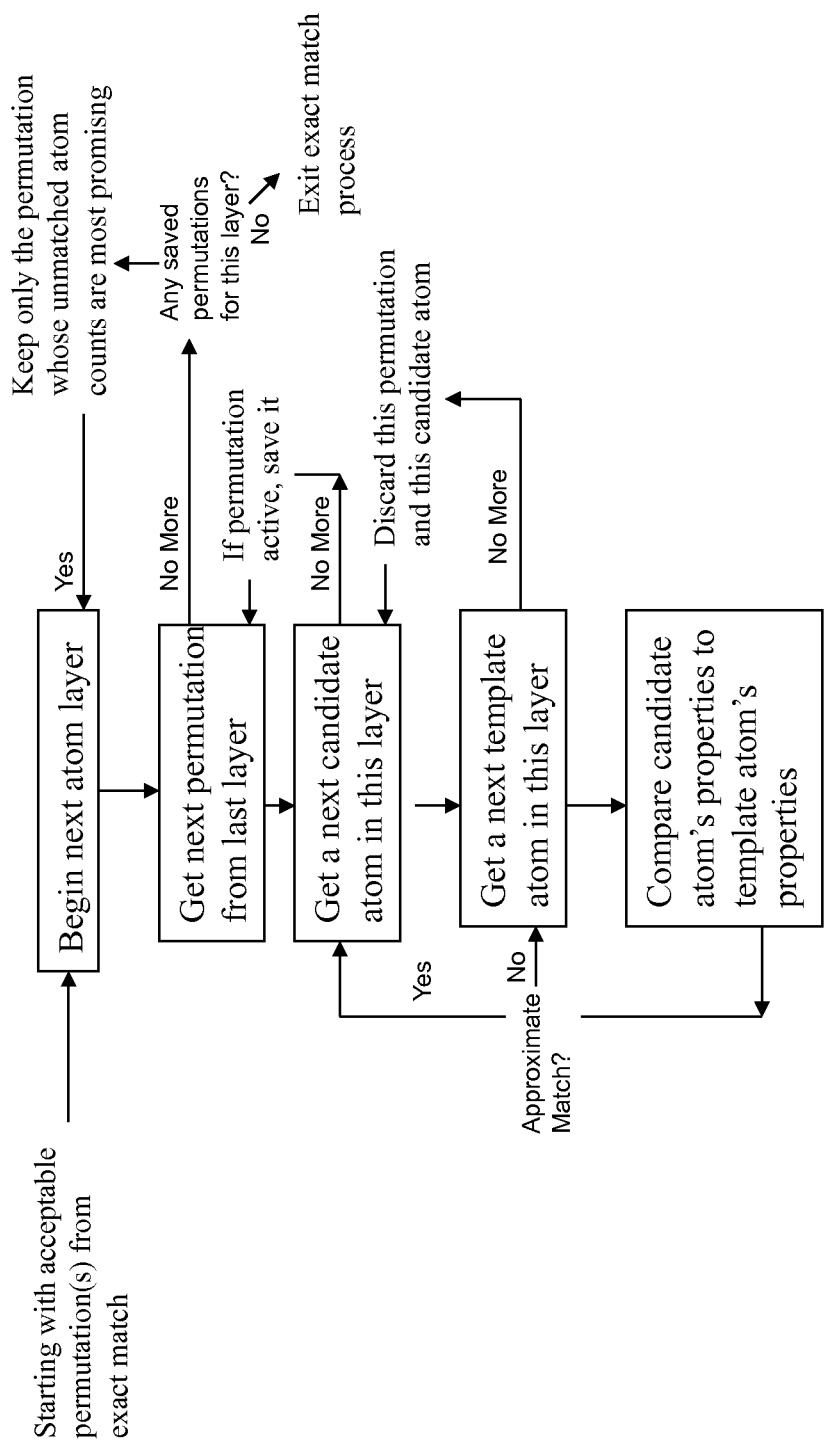
FIG. 2 provides a flow chart of the methodology of the present invention for an approximate match analysis.

The approximate mode comparison process is implemented as shown in the flow chart of FIG. 2 as follows:

Approximate Mode:
a) In "approximate" mode, any acyclic heavy atom in the candidate matches any heavy atom in the template. And, in order to ensure that the resulting candidate fragment can initially be positioned regardless of how well its atoms match those in the template, any candidate heavy atom will match any template heavy atom, regardless of any disagreement in atom or bond properties, until the processing of the fourth heavy atom layer begins.
A match to any cyclic heavy atom beyond the third layer of the candidate does require agreement in atom types and bond properties, just as in the exact mode. However, any of these three required classes of agreement can be deactivated by the user.

To prevent excessive proliferation of acceptable permutations, whenever a permutation generates multiple permutation offspring, only a single "most promising" permutation is retained. "Most promising" is defined as the permutation having the smallest sum of differences in the numbers of the still unmatched atoms within candidate and template, compared attached atom by attached atom.

When transitioning from "exact" to "approximate" mode, the set of potentially active permutations remaining from the "exact" mode is re-examined in the approximate mode.

The approximate mode and therefore step 4 terminates whenever any of the following conditions occurs:
a) all heavy atoms in the candidate have been matched to template heavy atoms
b) no heavy atoms in the template remain unmatched by candidate atoms
c) none of the permutations can be extended without violating an active atom or bond match criterion. At the completion of the approximate mode, the identification process is complete.

Step 5: Alignment of the Candidate Fragment:
a) A depth-first recursive processing of the candidate structure is undertaken, positioning each "current" atom as (or before, see below) it is encountered. This processing begins by simply copying the coordinates of the atoms defining the open "root" valence from the template to the candidate, both atoms becoming "positioned". The real atom of the two becomes the first "candidate" in the recursive processing.

For each newly encountered "candidate" atom:
a) Generate a list of the still unencountered atoms attached to this atom, and order these attachments so that no unmatched attachment atom is processed until all matched atoms have been. When this list has been completely processed, backtrack through the recursive tree until an atom having attachments that still need to be processed is encountered.
  i) If the attached atom has already been positioned (by any of the previous or following alignment operations), proceed immediately and recursively to the processing of its descendant atom, the already positioned atom now becoming the "current" atom.
  Otherwise:
  ii) If the bond between this atom and the "current" atom (its parent) is part of a ring while the bond between the atom in the previous atom layer (the parent) and the grandparent atom is non-cyclic, a new candidate ring system (possibly polycyclic, including multiple rings) has been encountered.
    (a) If such a new ring system is also encountered within the template fragment; and the newly encountered ring systems in candidate and template fragments contain the same number of atoms; and there is an exact 2D match between the atomic properties of the matching atoms that form the candidate and template fragment rings; then the 3D coordinates of the template ring atoms are copied to the candidate ring atoms and the candidate ring atoms are thereby positioned".
    (b) If the conditions in (a) above are not met, the candidate fragment ring atoms, also including all their more distant attachments, are reoriented to a least-squared distance overlay (have the same 3D orientation) with the smallest number of matching template fragment atoms that define a plane. (If there are insufficient matches, all of the candidate ring become "unmatched".) Because the initial 3D structures generated by Concord or Corina may provide different selections among possible ring "puckerings", all possible puckerings of the newly encountered ring atoms are generated, with the puckering that minimizes interatomic distances between candidate and template ring systems being retained. The candidate ring atoms thereby become positioned.
  iii) If the conditions of ii) above are not met, the bond between the atom and its parent atom is acyclic.
    a) If the new candidate fragment atom matches a template fragment atom, the coordinates of the template fragment atom are copied to the candidate atom and the candidate atom becomes positioned.

b) If the new candidate fragment atom does not match a template fragment atom, all the non-matching attachments to the "current" atom are put onto one list and all their matching template atoms are put onto a second list. Note that each of these attached atoms may be the start of a large branch, so each of these lists is first ordered by the number of heavy atoms that the attachment branch includes, largest to smallest. Then, proceeding in order down both of the lists, the new candidate fragment atom, also including all its more distant attachments, is positioned to exactly overlap its attachment bond (its bond to the "current atom") with the bond between the matching template atoms. If the template list is shorter than the candidate list, then the remaining candidate attachment atoms, including any more distant attached atoms, is positioned using the standard valence rules for the candidate "current atom".

Since the method fragments, aligns, and analyzes the predicted activity of each fragment from the database library on-the-fly, using the method of the present invention it is possible for a user to react constructively to observed changes in predicted activity; that is, the user may alter the alignment template to observe the effect on the predicted activities. This enables the user to take advantage of all experimental data indicating possible or alternate 3D alignments. It has been found in many cases that such an approach generates better results than a topomeric based approach. While topomers provide a consistent model, the use of actual 3D information provides an even more consistent model since the local templates are constrained to alignments that are known to be experimentally correct and have presumably been chosen to further ensure that local 3D similarity is maximized. The value of the method of the present invention is that the resulting CoMFA models provide extraordinarily accurate predictions of biological affinities, both desirable and undesirable, and therefore have a greater value in guiding lead optimization (the replacement of fragments from query molecules with identified fragments from database libraries). Finally, as noted above, in the case of non-congeneric series (chemically non-related molecules that exhibit activity at the same receptor), it is possible to align fragments across the non-congeneric series using the method of the present invention.

I claim:

1. A computer implemented drug discovery method utilizing a specifically programmed computer for aligning in three dimensions molecular fragments derived from molecules in a molecular database to a specified three dimensional template comprising the following steps:
   a) fragmenting a candidate template molecule;
   b) specifying the template fragment or fragments to which alignment is desired;
   c) fragmenting a molecular database molecule;
   d) specifying the database molecule fragment candidate that is to be aligned to a template fragment;
   e) generating 3D structures for the candidate fragment;
   f) orienting both the template and candidate fragments by superimposing each fragment attachment bond onto a fixed vector root position;
   g) identifying for both template and candidate fragments all atoms and atom/property types excluding all hydrogen atoms;
   h) matching identical atoms in the template and candidate fragments by sequential traversals of the fragments that start at the fragment root and end wherever no more identical matches exist along any branch;
   i) aligning the candidate fragment to the template fragment by assigning the coordinates of template atoms to the matching identical candidate atoms identified in step h;
   j) positioning any atoms in the candidate fragment that do not have matching atoms in the template fragment so as to maintain their relative positions to those atoms in the candidate fragment that had matching atoms in the template fragment;
   k) topomericaly aligning atoms in any branch that includes uncoordinated-copied atoms where the root of any branch will be a bond between a coordinate-copied and a coordinate-uncopied bond;
   l) outputting the candidate alignment if only one template fragment was generated in step b);
   m) repeating steps b) through h) for each additional template fragment that was generated in step b);
   n) selecting the alignment for the candidate fragment that has the largest number of atom-to-atom matches with a template fragment in step h); and
   o) outputting the candidate alignment.

2. The method of claim 1 in which in place of steps a) and b) the three dimensional coordinates of a template are user specified.

3. A computer implemented drug discovery method utilizing a specifically programmed computer in which selection of a substitute fragment is made for a fragment in a lead compound based on the predicted activity of a molecule incorporating the substitute fragment comprising the following steps:
   a) identifying a 3D template fragment from the lead compound;
   b) fragmenting molecules in a molecular database;
   c) aligning 3D database fragments to the lead compound template fragment by
   assigning, where appropriate, 3D coordinates of the template fragment atoms to the database fragment atoms;
   d) characterizing the shape of the aligned database fragments;
   e) arranging the shape characterizations in a data table;
   f) performing a 3D QSAR CoMFA analysis on the data table to predict likely activities; and
   g) selecting the molecular database fragment with the greatest likely activity for substitution in the lead compound.

* * * * *